United States Patent
Sasaki et al.

(10) Patent No.: US 12,133,768 B2
(45) Date of Patent: Nov. 5, 2024

(54) ULTRASONIC DIAGNOSTIC APPARATUS, MEDICAL IMAGING APPARATUS, TRAINING DEVICE, ULTRASONIC IMAGE DISPLAY METHOD, AND STORAGE MEDIUM

(71) Applicant: CANON KABUSHIKI KAISHA, Tokyo (JP)

(72) Inventors: Shoya Sasaki, Kanagawa (JP); Yoshinori Hirano, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/103,756

(22) Filed: Nov. 24, 2020

(65) Prior Publication Data

US 2021/0161510 A1 Jun. 3, 2021

(30) Foreign Application Priority Data

Nov. 28, 2019 (JP) .................... 2019-215796

(51) Int. Cl.
*A61B 8/00* (2006.01)
*A61B 8/06* (2006.01)
*A61B 8/08* (2006.01)
*G06N 3/08* (2023.01)

(52) U.S. Cl.
CPC .............. *A61B 8/5207* (2013.01); *A61B 8/06* (2013.01); *A61B 8/464* (2013.01); *A61B 8/469* (2013.01); *A61B 8/485* (2013.01); *G06N 3/08* (2013.01)

(58) Field of Classification Search
CPC ......... A61B 8/5207; A61B 8/06; A61B 8/464; A61B 8/469; A61B 8/485; A61B 8/08; A61B 8/0891; A61B 8/461; A61B 8/5223; A61B 8/488; G06N 3/08; G06N 3/0454; G06N 20/10; G06N 3/045
See application file for complete search history.

(56) References Cited

U.S. PATENT DOCUMENTS

| 2010/0069756 A1* | 3/2010 | Ogasawara | A61B 8/08 600/447 |
|---|---|---|---|
| 2012/0095341 A1* | 4/2012 | Shiki | A61B 8/06 600/443 |
| 2014/0031690 A1* | 1/2014 | Toji | A61B 8/06 600/443 |

(Continued)

FOREIGN PATENT DOCUMENTS

| JP | 2019000151 A | 1/2019 | |
|---|---|---|---|
| WO | WO-2018094118 A1 * | 5/2018 | ............... A61B 8/12 |
| WO | WO-2018215641 A1 * | 11/2018 | ............... A61B 8/06 |

*Primary Examiner* — Joseph M Santos Rodriguez
(74) *Attorney, Agent, or Firm* — Canon U.S.A., Inc. IP Division

(57) ABSTRACT

An ultrasonic diagnostic apparatus, a medical imaging apparatus, a training device, an ultrasonic image display method, and a storage medium storing a program that can quickly set a region of interest on an ultrasonic image are provided. The ultrasonic diagnostic apparatus includes an ultrasonic image generation unit configured to generate an ultrasonic image of a subject, an inference unit configured to set, by using a trained model trained with a region of interest set on the ultrasonic image as teaching data, a region of interest on a new generated ultrasonic image, and a display unit configured to display the region of interest set by the inference unit along with the new generated ultrasonic image.

18 Claims, 12 Drawing Sheets

(56) References Cited

U.S. PATENT DOCUMENTS

| | | | |
|---|---|---|---|
| 2015/0112182 A1* | 4/2015 | Sharma | A61B 5/0261 |
| | | | 600/408 |
| 2016/0000408 A1* | 1/2016 | Matsunaga | A61B 8/463 |
| | | | 600/443 |
| 2017/0360412 A1* | 12/2017 | Rothberg | G06T 7/0012 |
| 2018/0190377 A1* | 7/2018 | Schneemann | G06V 10/454 |
| 2019/0261949 A1* | 8/2019 | Labyed | G06T 7/0012 |
| 2019/0333210 A1* | 10/2019 | Mihalef | A61B 8/488 |
| 2019/0336101 A1* | 11/2019 | Chiang | A61B 1/00 |
| 2019/0336107 A1* | 11/2019 | Hope Simpson | G06T 7/0012 |

* cited by examiner

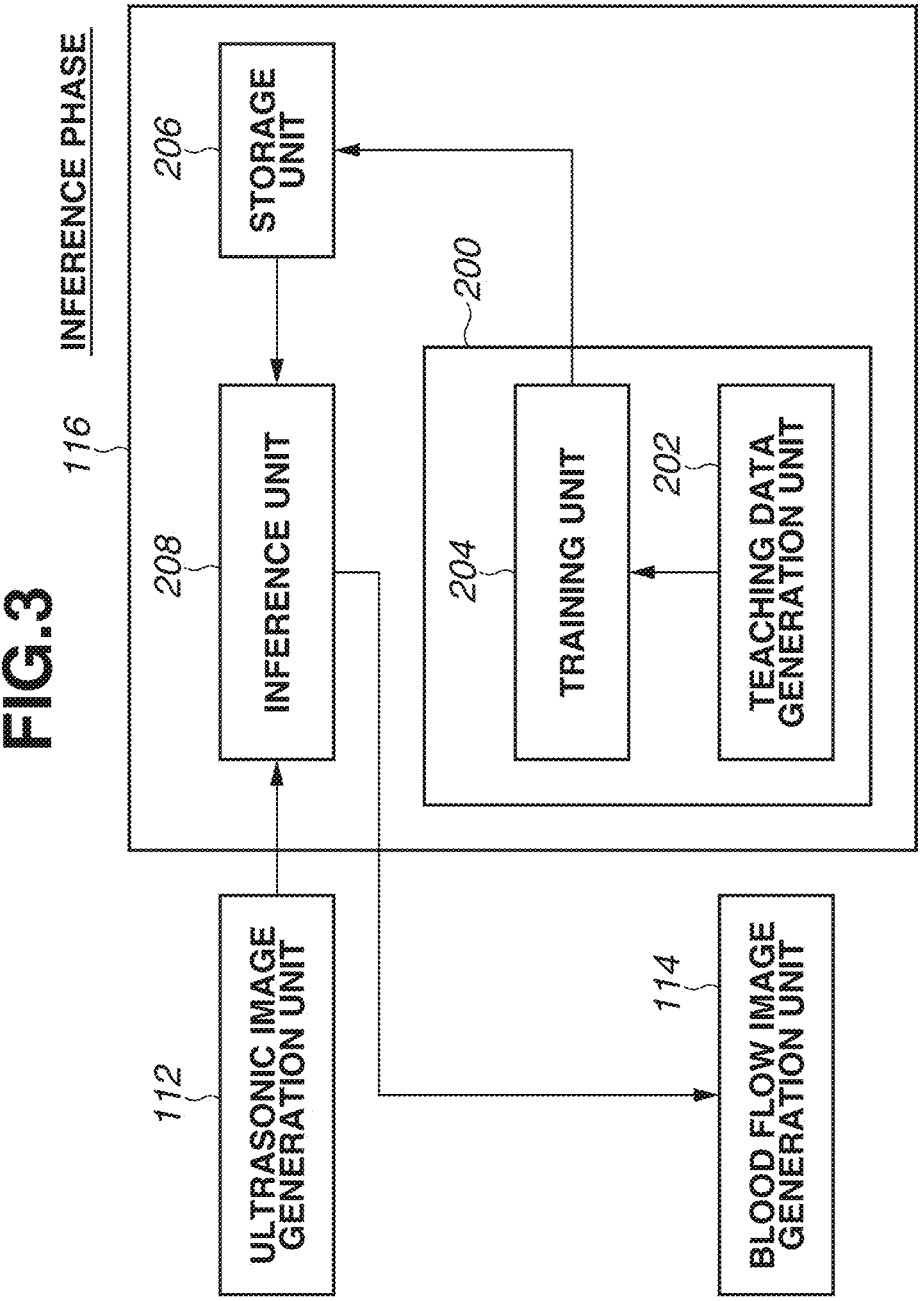

ULTRASONIC DIAGNOSTIC APPARATUS, MEDICAL IMAGING APPARATUS, TRAINING DEVICE, ULTRASONIC IMAGE DISPLAY METHOD, AND STORAGE MEDIUM

BACKGROUND OF THE DISCLOSURE

Field of the Disclosure

The present disclosure relates to an ultrasonic diagnostic apparatus, a medical imaging apparatus, a training device, an ultrasonic image display method, and a storage medium for setting a region of interest on a medical image such as an ultrasonic image.

Description of the Related Art

In observing an ultrasonic image, a region of interest can be set, for example, so that a region where a blood flow exists is included for the sake of blood flow inspection or a region where a lesion exists is included for the sake of lesion inspection.

Japanese Patent Application Laid-Open No. 2019-151 discusses calculating representative points of a blood flow region based on combined blood flow data, and setting a region of interest based on the representative points. The combined blood flow data is obtained by combining a plurality of pieces of blood flow data obtained by repeated scanning of steered ultrasonic waves.

According to Japanese Patent Application Laid-Open No. 2019-151, to set a region of interest, the steered ultrasonic waves are repeatedly scanned before the calculation of the combined blood flow data. It therefore takes a long time to set a region of interest.

SUMMARY OF THE DISCLOSURE

The present disclosure is directed to providing an ultrasonic diagnostic apparatus (medical imaging apparatus) that can quickly set a region of interest on a medical image such as an ultrasonic image.

According to an aspect of the present invention, an ultrasonic diagnostic apparatus includes an ultrasonic image generation unit configured to generate an ultrasonic image of a subject, an inference unit configured to set, by using a trained model trained with a region of interest set on the ultrasonic image as teaching data, a region of interest on a new generated ultrasonic image, and a display unit configured to display the region of interest set by the inference unit along with the new generated ultrasonic image.

Further features of the present disclosure will become apparent from the following description of exemplary embodiments with reference to the attached drawings.

BRIEF DESCRIPTION OF THE DRAWINGS

FIG. 3 is a diagram illustrating a configuration of the region of interest setting unit of the ultrasonic diagnostic apparatus according to the present exemplary embodiment.

DESCRIPTION OF THE EMBODIMENTS

Exemplary embodiments of the present invention will be described below with reference to the accompanying drawings.

Figure 1:
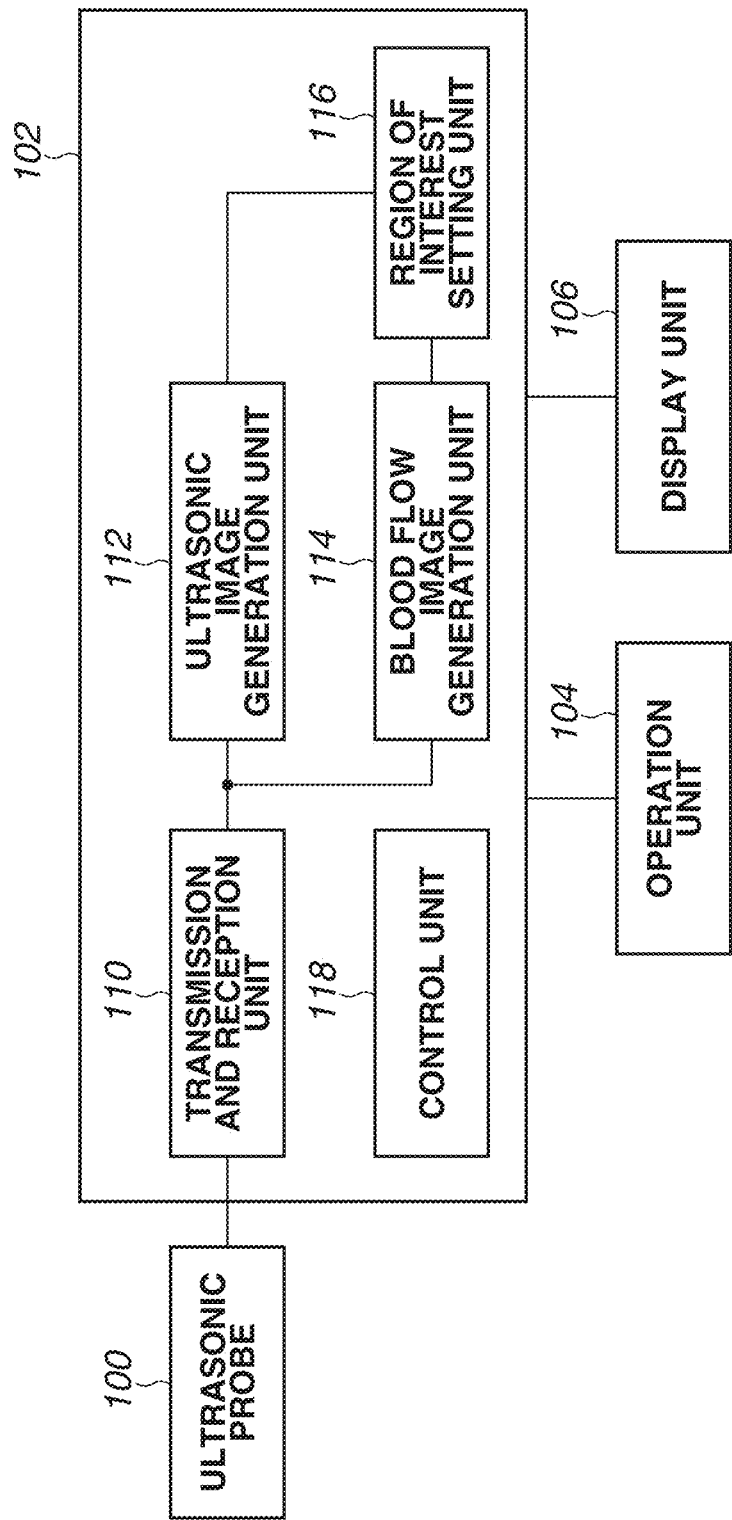
FIG. 1 is a diagram illustrating a configuration of an ultrasonic diagnostic apparatus according to a first exemplary embodiment of the present invention.

FIG. 1 illustrates a configuration of an ultrasonic diagnostic apparatus according to a first exemplary embodiment of the present invention. The ultrasonic diagnostic apparatus includes an ultrasonic probe 100, an apparatus main body 102, an operation unit 104, and a display unit 106. The ultrasonic probe 100 is brought into contact with a subject, and transmits and receives ultrasonic waves. The apparatus main body 102 processes an ultrasonic wave signal received by the ultrasonic probe 100 to generate an ultrasonic image, and performs various types of measurement. The operation unit 104 is intended to operate the apparatus main body 102. The display unit 106 displays the ultrasonic image and measurement results.

The ultrasonic probe 100 is connected to the apparatus main body 102. The ultrasonic probe 100 includes a plurality of transducers and can generate ultrasonic waves by driving the plurality of transducers. The ultrasonic probe 100 receives reflected waves from the subject and converts the reflected waves into an electrical signal. The converted electrical signal is transmitted to the apparatus main body 102.

The ultrasonic probe 100 also includes an acoustic matching layer and a backing material. The acoustic matching layer is located on the front side (subject side) of the plurality of transducers and matches acoustic impedance of the plurality of transducers with that of the subject. The backing material is located on the back side of the plurality of transducers and prevents propagation of ultrasonic waves from the plurality of transducers to the back side.

The ultrasonic probe 100 is detachably connected to the apparatus main body 102. Possible types of ultrasonic probes 100 include linear, sector, convex, radial, and three-dimensional scanning ultrasonic probes. The operator can select a type of ultrasonic probe 100 based on the imaging purpose.

The apparatus main body 102 includes a transmission and reception unit 110, an ultrasonic image generation unit 112, a blood flow image generation unit 114, a region of interest setting unit 116, and a control unit 118. The transmission and reception unit 110 makes the ultrasonic probe 100 transmit and receive ultrasonic waves. The ultrasonic image generation unit 112 generates an ultrasonic image by using an ultrasonic wave signal received by the transmission and reception unit 110. The blood flow image generation unit 114 generates a blood flow image by using the ultrasonic wave signal received by the transmission and reception unit 110. The region of interest setting unit 116 sets a region of interest on the ultrasonic image. The control unit 118 controls various components of the apparatus main body 102.

The transmission and reception unit 110 controls the transmission and reception of ultrasonic waves to be performed by the ultrasonic probe 100. The transmission and reception unit 110 includes a pulse generation unit and a transmission delay circuit, and supplies a driving signal to the ultrasonic probe 100. The pulse generation unit repeatedly generates rate pulses at a predetermined repetition frequency (pulse repetition frequency (PRF)). The transmission delay circuit gives the rate pulses generated by the pulse generation unit a delay time for focusing ultrasonic waves generated from the ultrasonic probe 100 to determine transmission directivity. The transmission delay circuit can control the transmission direction of the ultrasonic waves transmitted from the transducers by changing the delay time to be given to the rate pulses.

The transmission and reception unit 110 also includes an amplifier, an analog-to-digital (A/D) conversion unit, a reception delay circuit, and an addition unit. The transmission and reception unit 110 generates an ultrasonic wave signal by performing various types of processing on a reflected wave signal received by the ultrasonic probe 100. The amplifier amplifies the reflected wave signal channel by channel to perform gain correction processing. The A/D conversion unit A/D-converts the gain-corrected reflected wave signal. The reception delay circuit gives the resulting digital data a delay time for determining reception directivity. The addition unit performs addition processing of reflected wave signals to which delay times are given by the reception delay circuit. The addition processing by the addition unit enhances reflection components in a direction corresponding to the reception directivity of the reflected wave signals.

In two-dimensionally scanning the subject, the transmission and reception unit 110 makes the ultrasonic probe 100 transmit two-dimensional ultrasonic waves. The transmission and reception unit 110 then generates a two-dimensional ultrasonic wave signal from a two-dimensional reflected wave signal received by the ultrasonic probe 100. In three-dimensionally scanning the subject, the transmission and reception unit 110 makes the ultrasonic probe 100 transmit three-dimensional ultrasonic waves. The transmission and reception unit 110 then generates a three-dimensional ultrasonic wave signal from a three-dimensional reflected wave signal received by the ultrasonic probe 100.

The ultrasonic image generation unit 112 performs various types of signal processing on the ultrasonic wave signal output from the transmission and reception unit 110 to generate an ultrasonic image. The ultrasonic image generation unit 112 performs signal processing such as detection processing and logarithmic compression on the ultrasonic wave signal to generate an ultrasonic image (brightness mode (B-mode) image) where a signal intensity is expressed in terms of brightness.

The blood flow image generation unit 114 can generate a blood flow image by a color Doppler method called color flow mapping (CFM). The color Doppler method can extract motion information about a blood flow by transmitting ultrasonic waves in the same direction a plurality of times and performing a Doppler effect-based frequency analysis on the received reflected wave signal. The blood flow image generation unit 114 generates blood flow information such as an average speed, dispersion, and power in the form of a blood flow image by using the color Doppler method. Alternatively, the blood flow image generation unit 114 may generate a blood flow image by a power Doppler method.

The region of interest setting unit 116 sets a region to generate a blood flow image in the ultrasonic image generated by the ultrasonic image generation unit 112 as a region of interest. The region of interest (region coordinates) set by the region of interest setting unit 116 is transmitted to the blood flow image generation unit 114. The blood flow image generation unit 114 generates a blood flow image for the region of interest set by the region of interest setting unit 116 by the color Doppler method. The blood flow image is thus generated for the region of interest set by the region of interest setting unit 116. Setting the region of interest by the region of interest setting unit 116 can narrow the region to transmit ultrasonic waves for generating a blood flow image in the same direction a plurality of times, and can enhance the frame rate of the ultrasonic image and the blood flow image. A high frame rate can be achieved by the region of interest setting unit 116 setting the region of interest to a minimum.

The operation unit 104 includes a mouse, a keyboard, a button, a panel switch, a touch command screen, a foot switch, a track ball, and/or a joystick. The operation unit 104 accepts various instructions from the operator of the ultrasonic diagnostic apparatus, and transmits the accepted various instructions to the apparatus main body 102.

The display unit 106 displays a graphical user interface (GUI) for the operator of the ultrasonic diagnostic apparatus to input various instructions by using the operation unit 104. The display unit 106 also displays ultrasonic images, blood flow images, and measurement results generated by the apparatus main body 102.

If a region of interest for generating a blood flow image is set by the region of interest setting unit 116, the display unit 106 displays a blood flow image generated by the blood flow image generation unit 114 as superimposed on an ultrasonic image generated by the ultrasonic image generation unit 112. Within the region of interest set by the region of interest setting unit 116, the ultrasonic image and the blood flow image are displayed. Outside the region of interest, only the ultrasonic image is displayed.

The transmission and reception unit 110, the ultrasonic image generation unit 112, the blood flow image generation unit 114, and the region of interest setting unit 116 of the apparatus main body 102 may be configured by hardware such as an integrated circuit, or by software modules or programs.

In the case of an ordinary ultrasonic diagnostic apparatus, the operator manually sets a region of interest via an operation unit (region of interest setting unit) while observing a specific region of an ultrasonic image. By contrast, the ultrasonic diagnostic apparatus according to the present exemplary embodiment can set a region of interest on a specific region by using a trained model trained to set a region of interest on the specific region. The region of interest is set to cover part of the specific region. An example of the trained model is a trained neural network. Any models such as a deep learning model and a support vector machine may be used. The trained model may be stored in the region of interest setting unit 116, or connected to the ultrasonic diagnostic apparatus via a network.

Specifically, the region of interest setting unit 116 generates the trained model by performing training with a region of interest set on a blood flow region of an ultrasonic image as teaching data. Using the trained model, the region of interest setting unit 116 identifies a blood flow region in a new generated ultrasonic image and sets a region of interest on the blood flow region. The region of interest set by the region of interest setting unit 116 is set on the ultrasonic image. The blood flow image generation unit 114 generates a blood flow image for the region of interest set by the region of interest setting unit 116 by the color Doppler method.

The ultrasonic image input to the region of interest setting unit 116 (trained model) may be two-dimensional image data or three-dimensional image data (volume data).

As described above, the trained model is trained to set a region of interest. A model for identifying a blood flow region from two-dimensional image data and setting a region of interest may be used. A model for identifying a blood flow region from three-dimensional image data and setting a region of interest may be used.

Figure 2:
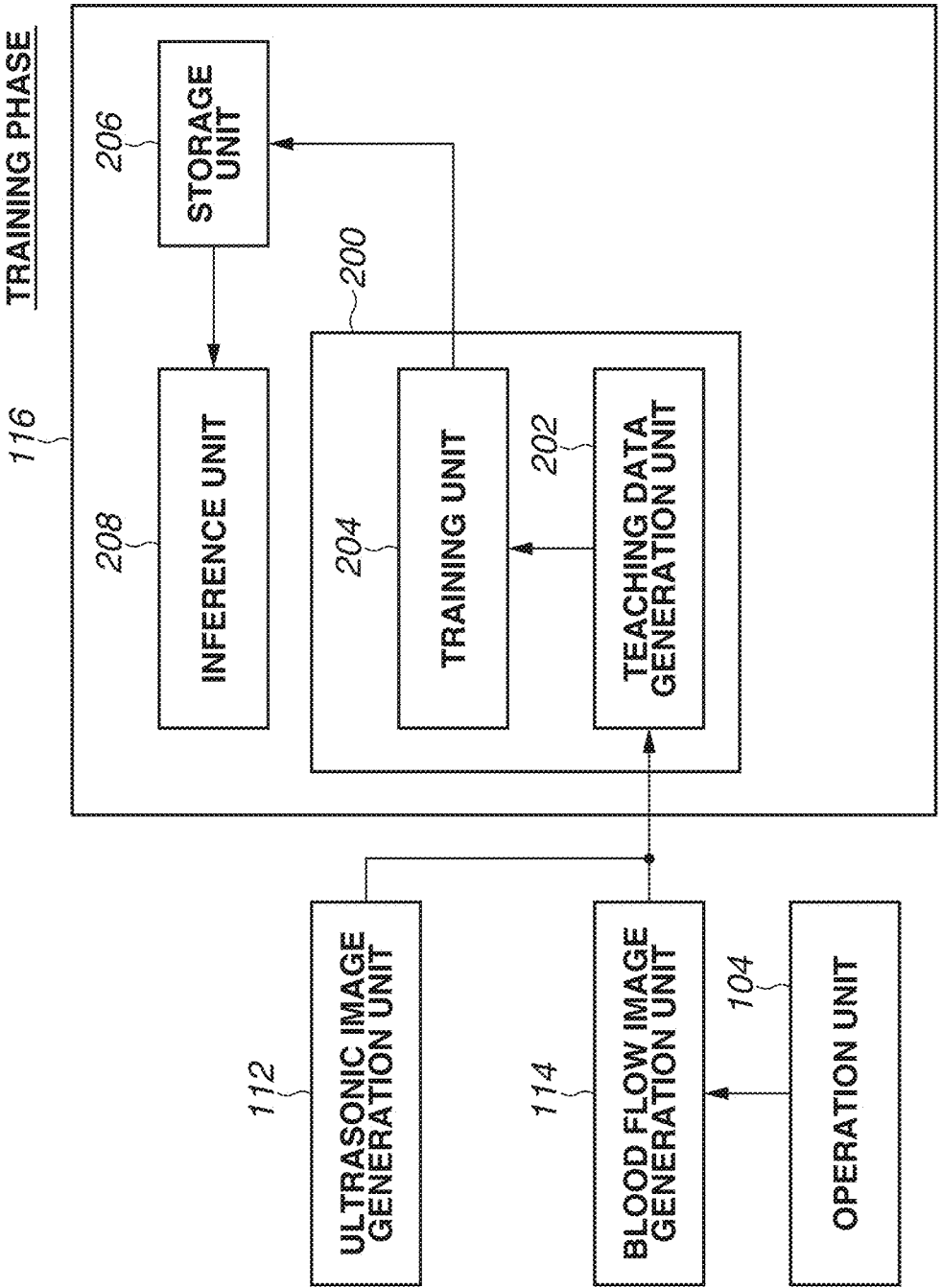
FIG. 2 is a diagram illustrating a configuration of a region of interest setting unit of the ultrasonic diagnostic apparatus according to the present exemplary embodiment.

Details of the region of interest setting unit 116 in the ultrasonic diagnostic apparatus according to the present exemplary embodiment will be described with reference to FIGS. 2 and 3. In FIGS. 2 and 3, the region of interest setting unit 116 has the same configuration. The reason why different diagrams are used is to distinguish an operation in a training phase from that in an inference phase. FIG. 2 illustrates the operation of the region of interest setting unit 116 in the training phase. FIG. 3 illustrates the operation of the region of interest setting unit 116 in the inference phase.

The region of interest setting unit 116 includes a training device 200, a storage unit 206, and an inference unit 208. The training device 200 generates a trained model by performing training with a region of interest on a blood flow region of an ultrasonic image as teaching data. The storage unit 206 stores the trained model generated by the training device 200. The inference unit 208 identifies a blood flow region in an ultrasonic image and sets (infers) a region of interest on the blood flow region by using the trained model.

The training device 200 trains the model to learn a region of interest on a blood flow region of an ultrasonic image by using teaching data including a region of interest set on an ultrasonic image. The region of interest serving as the teaching data is set on the blood flow region of an ultrasonic image. The teaching data may include the ultrasonic image.

The training device 200 includes a teaching data generation unit 202 and a training unit 204. The teaching data generation unit 202 generates teaching data about a region of interest on a blood flow region of an ultrasonic image. The training unit 204 trains the model to learn a region of interest on a blood flow region of an ultrasonic image by using the teaching data generated by the teaching data generation unit 202.

A plurality of ultrasonic images captured in the past and regions of interest set on the respective plurality of ultrasonic images are stored in a memory of the training device 200. The training device 200 performs training with the regions of interest on the respective plurality of ultrasonic images stored in the memory as teaching data.

The operation unit 104 includes a freeze button for freezing (stopping) an ultrasonic image displayed in real time in storing the ultrasonic image. The operator can freeze the ultrasonic image displayed in real time on the display unit 106 by pressing the freeze button while holding the ultrasonic probe 100 still. The frozen ultrasonic image can be stored in the ultrasonic diagnostic apparatus.

If there is a region of interest set on the frozen ultrasonic image on the display unit 106 at the timing when the freeze button of the operation unit 104 is pressed by the operator, the frozen ultrasonic image displayed on the display unit 106 and the region of interest are output to the training device 200. The reason why the frozen ultrasonic image is output to the training device 200 is that the ultrasonic image is a still image suitable for training by the training device 200.

The training device 200 can also determine whether a region of interest is set on the frozen ultrasonic image on the display unit 106, based on an ultrasonic imaging mode. For example, if the ultrasonic imaging mode is a blood flow mode (CFM), the training device 200 can determine that a region of interest is set on the ultrasonic image. The training device 200 can then store the ultrasonic image and the region of interest in association with each other, and performs training with the region of interest on the ultrasonic image as teaching data.

For example, the training unit 204 uses a neural network, which includes a plurality of layers. The plurality of layers includes an input layer, an output layer, and a plurality of intermediate layers therebetween. Although not illustrated in the drawings, the plurality of intermediate layers includes a convolutional layer, a pooling layer, an upsampling layer, and a combination layer. The convolutional layer is a layer for performing convolution processing on a group of input values. In the convolutional layer, the input ultrasonic image (region of interest) is convolved to extract features of the ultrasonic image (region of interest).

The pooling layer is a layer for performing processing for reducing the number of groups of output values compared to that of groups of input values by decimating or combining the groups of input values. The upsampling layer is a layer for performing processing for increasing the number of groups of output values compared to that of groups of input values by duplicating the groups of input values or adding values interpolated from the groups of input values. The combination layer is a layer for performing processing for inputting groups of values, such as a group of output values of a layer and a group of pixel values constituting an ultrasonic image (region of interest), from a plurality of sources and combining the groups of values by connecting or adding the groups of values. The number of intermediate layers can be changed at any time based on the training contents.

In such a manner, the training device 200 (training unit 204) generates a trained model by training a neural network in association with a region of interest on an ultrasonic image as teaching data.

Figure 4A:
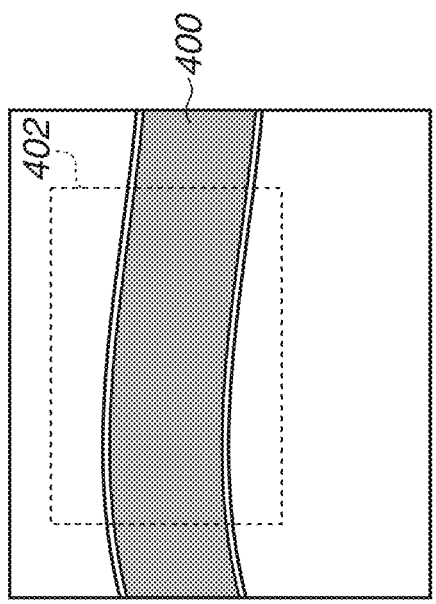
FIGS. 4A to 4C are diagrams illustrating examples of an ultrasonic image output to a training device according to the present exemplary embodiment.
Figure 4B:
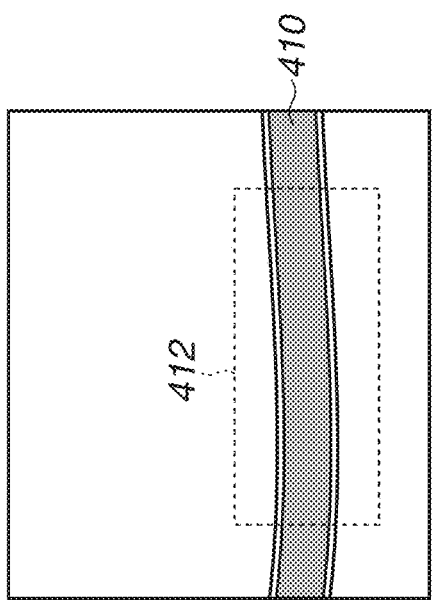
Figure 4C:
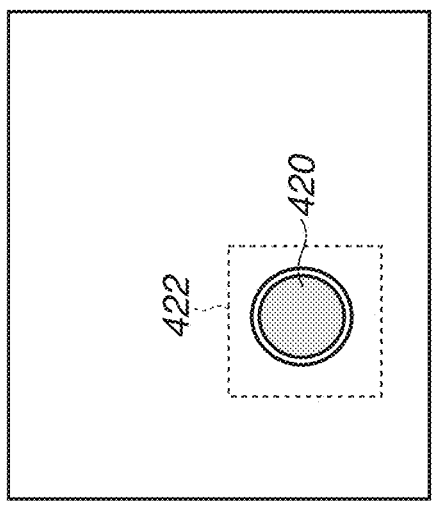

FIGS. 4A to 4C illustrate examples of an ultrasonic image output to the training device 200. FIG. 4A illustrates an ultrasonic image where a region of interest 402 is set on a longitudinal sectional blood flow region 400. A blood flow image is generated for the region surrounded by the region of interest 402 by the color Doppler method. The training unit 204 performs training with the region of interest 402 on the ultrasonic image (blood flow region 400) as teaching data.

The region of interest 402 used as the teaching data may be information indicating the region coordinates (for example, coordinates of four points) of the region of interest 402 in the ultrasonic image. The region of interest 402 used as the teaching data may be the region coordinates input to the operation unit 104 to set the region of interest 402.

Similarly, FIG. 4B illustrates an ultrasonic image where a region of interest 412 is set on a longitudinal sectional blood flow region 410. A blood flow image is generated for a region surrounded by the region of interest 412 by the color Doppler method. The training unit 204 performs training with the region of interest 412 on the ultrasonic image (blood flow region 410) as teaching data.

FIG. 4C illustrates an ultrasonic image where a region of interest 422 is set on a cross-sectional blood flow region 420. A blood flow image is generated for a region surrounded by the region of interest 422 by the color Doppler method. The training unit 204 performs training with the region of interest 422 on the ultrasonic image (blood flow region 420) as teaching data.

In such a manner, the training unit 204 can train a model with features (such as a position and a size) of a region of interest actually set on an ultrasonic image. The training unit 204 can train a model by using as the teaching data a region of interest that is a region where a blood flow image is generated regardless of the type of blood vessel drawn in the ultrasonic image.

The training device 200 trains the model to learn a region of interest on a blood flow region of an ultrasonic image by using teaching data including the blood flow region of the ultrasonic image and the region of interest set on the ultrasonic image. For example, the training device 200 generates a trained model by performing training with the blood flow region on the ultrasonic image and the region of interest set on the ultrasonic image as teaching data. Here, the region of interest can be learned in association with the blood flow region of the ultrasonic image.

FIG. 4A illustrates the ultrasonic image where the region of interest 402 is set on the longitudinal sectional blood flow region 400. The training unit 204 performs training with the blood flow region 400 of the ultrasonic image and the region of interest 402 on the blood flow region 400 as teaching data.

The training unit 204 extracts the blood flow region 400 from the ultrasonic image by using a segmentation technique (such as region growing and level setting). In such a case, the blood flow region 400 used as the teaching data is information indicating the region coordinates of the blood flow region 400 extracted from the ultrasonic image.

The operator may input information indicating the region coordinates of the blood flow region 400 into the operation unit 104, and the training unit 204 may extract the blood flow region 400 from the ultrasonic image based on the information. In such a case, the blood flow region 400 used as the teaching data is the information indicating the region coordinates input to the operation unit 104.

FIG. 4B illustrates the ultrasonic image where the region of interest 412 is set on the longitudinal sectional blood flow region 410. The training unit 204 performs training with the blood flow region 410 of the ultrasonic image and the region of interest 412 on the blood flow region 410 as teaching data.

Similarly, FIG. 4C illustrates the ultrasonic image where the region of interest 422 is set on the cross-sectional blood flow region 420. The training unit 204 performs training with the blood flow region 420 of the ultrasonic image and the region of interest 422 on the blood flow region 420 as teaching data.

In such a manner, the training unit 204 can train a model with features (such as positions and sizes) of the regions of interest actually set on various blood flow regions of ultrasonic images.

The training device 200 may train the model to learn a region of interest on a blood region of an ultrasonic image by using teaching data including the blood flow region of the ultrasonic image. For example, the training device 200 generates a trained model by performing training with a blood flow region of an ultrasonic image as teaching data. The reason is that if a blood flow region can be identified in an ultrasonic image, a region of interest is typically set to cover the blood flow region.

FIG. 4A illustrates the ultrasonic image where the region of interest 402 is set on the longitudinal sectional blood flow region 400. The training unit 204 performs training with the blood flow region 400 of the ultrasonic image as teaching data. The training unit 204 extracts the blood flow region 400 from the ultrasonic image by using a segmentation technique (such as region growing and level setting). In such a case, the blood flow region 400 used as the teaching data is information indicating the region coordinates of the blood flow region 400 extracted from the ultrasonic image.

FIG. 4B illustrates the ultrasonic image where the region of interest 412 is set on the longitudinal sectional blood flow region 410. The training unit 204 performs training with the blood flow region 410 of the ultrasonic image as teaching data. Similarly, FIG. 4C illustrates the ultrasonic image where the region of interest 422 is set on the cross-sectional blood flow region 420. The training unit 204 performs training with the blood flow region 420 of the ultrasonic image as teaching data.

Figure 5:
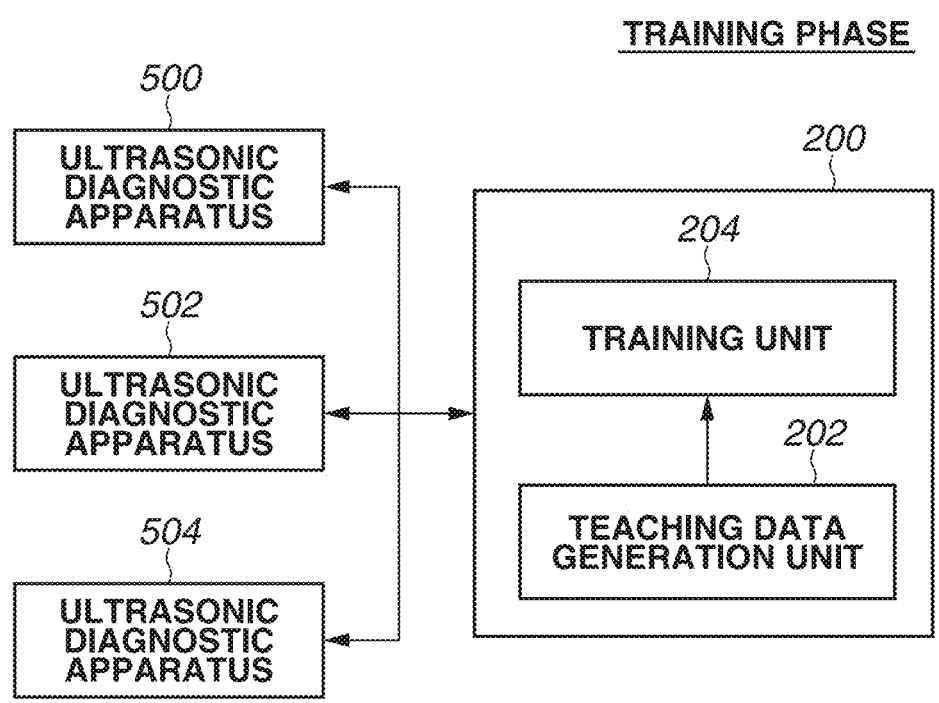
FIG. 5 is a diagram illustrating an example where the training device according to the present exemplary embodiment is installed outside ultrasonic diagnostic apparatuses.

The training device 200 may be installed outside the ultrasonic diagnostic apparatus. FIG. 5 illustrates an example where the training device 200 is installed outside ultrasonic diagnostic apparatuses.

For example, the training device 200 may be located on an in-hospital network or on a cloud network outside the hospital. A plurality of ultrasonic diagnostic apparatuses 500, 502, and 504 is connected to the training device 200. While three ultrasonic diagnostic apparatuses are illustrated as the plurality of ultrasonic diagnostic apparatuses here, the plurality of ultrasonic diagnostic apparatuses may include four or more ultrasonic diagnostic apparatuses.

For example, the training device 200 generates a trained model by performing training with a region of interest on an ultrasonic image captured by the ultrasonic diagnostic apparatus 500 as teaching data. The training device 200 updates the trained model by performing training with a region of interest on an ultrasonic image captured by the ultrasonic diagnostic apparatus 502 different from the ultrasonic diagnostic apparatus 500 as teaching data. Similarly, the training device 200 updates the trained model by performing training with a region of interest on an ultrasonic image captured by the ultrasonic diagnostic apparatus 504 different from the ultrasonic diagnostic apparatuses 500 and 502 as teaching data. The trained model generated (updated) by the training device 200 is transmitted to each of the plurality of ultrasonic diagnostic apparatuses 500, 502, and 504. The plurality of ultrasonic diagnostic apparatuses 500, 502, and 504 each stores the latest trained model generated (updated) by the training device 200.

As described above, the training device 200 can perform training with the regions of interest set by the plurality of ultrasonic diagnostic apparatuses 500, 502, and 504 as teaching data. The training device 200 can thus generate a trained model corresponding to the plurality of ultrasonic diagnostic apparatuses 500, 502, and 504.

The training device 200 can also perform training with blood flow regions of ultrasonic images captured by the plurality of ultrasonic diagnostic apparatuses 500, 502, and 504 and regions of interest on the blood flow regions as teaching data.

The region of interest setting unit 116 in the inference phase will be described with reference to FIG. 3.

The storage unit 206 is connected to the training device 200. The storage unit 206 stores a trained model trained to set a region of interest on an ultrasonic image. Specifically, the storage unit 206 stores a trained model trained to identify a specific region from an ultrasonic image and set a region of interest on the specific region.

A new ultrasonic image generated by the ultrasonic image generation unit 112 is output to the inference unit 208. The inference unit 208 sets a region of interest on the new generated ultrasonic image by using the trained model trained to set a region of interest on an ultrasonic image.

The inference unit 208 can also determine the presence or absence of a blood flow region in an ultrasonic image. An example of the timing to determine the presence or absence of a blood flow region in an ultrasonic image is when the freeze button of the operation unit 104 is pressed. The setting of the region of interest by the inference unit 208 is controlled based on the presence or absence of a blood flow region in the ultrasonic image.

If the new generated ultrasonic image includes a blood flow region, the inference unit 208 sets a region of interest on the new generated ultrasonic image by using the trained model trained to set a region of interest on an ultrasonic image. The region of interest set by the inference unit 208 is transmitted to the blood flow image generation unit 114. The blood flow image generation unit 114 generates a blood flow image for the region of interest set by the region of interest setting unit 116 by the color Doppler method. The display unit 106 displays the blood flow image generated by the blood flow image generation unit 114 as superimposed on the ultrasonic image generated by the ultrasonic image generation unit 112.

If the new generated ultrasonic image does not include a blood flow region, the inference unit 208 does not set a region of interest on the new generated ultrasonic image. The display unit 106 displays only the ultrasonic image generated by the ultrasonic image generation unit 112.

Figure 6:
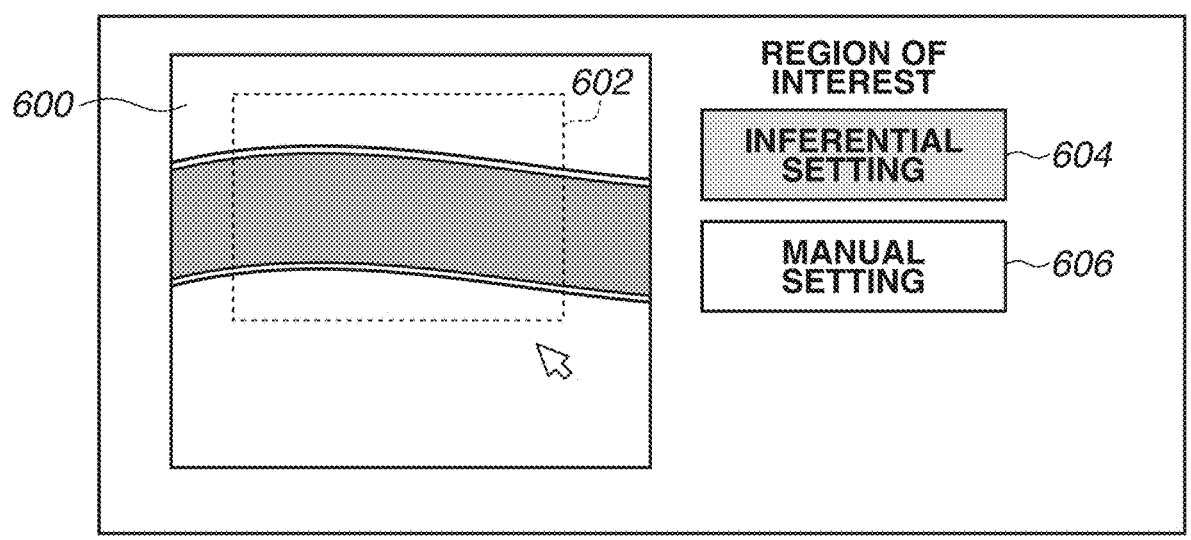
FIG. 6 is a diagram illustrating a display mode of a display unit of the ultrasonic diagnostic apparatus according to the present exemplary embodiment.

Next, a display mode of the display unit 106 of the ultrasonic diagnostic apparatus will be described with reference to FIG. 6. An inferential setting button 604 for setting a region of interest by inference and a manual setting button 606 for manually setting a region of interest are displayed. The inferential setting button 604 and the manual setting button 606 correspond to the operation unit 104. The inferential setting button 604 and the manual setting button 606 are displayed as icons on the display unit 106. The operator can select either one of the inferential setting button 604 and the manual setting button 606.

If the inferential setting button 604 is pressed by the operator, the inference unit 208 sets a region of interest 602 on an ultrasonic image 600 displayed on the display unit 106 by using the trained model trained to set a region of interest on an ultrasonic image. The inferential setting button 604 may be pressed by default.

The region of interest 602 set by the inference unit 208 is transmitted to the blood flow image generation unit 114. The blood flow image generation unit 114 generates a blood flow image for the region of interest 602 set by the inference unit 208 by the color Doppler method. The display unit 106 displays the blood flow image generated by the blood flow image generation unit 114 as superimposed on the ultrasonic image 600 generated by the ultrasonic image generation unit 112.

If the manual setting button 606 is pressed by the operator, the operator manually sets the region of interest 602 via the operation unit 104 (region of interest setting unit 116) while observing a specific region of the ultrasonic image 600.

If the operator wants to adjust the region of interest 602 set by the inference unit 208, the operator can adjust the region of interest 602 via the operation unit 104 (region of interest setting unit 116) by pressing the manual setting button 606.

Figure 7:
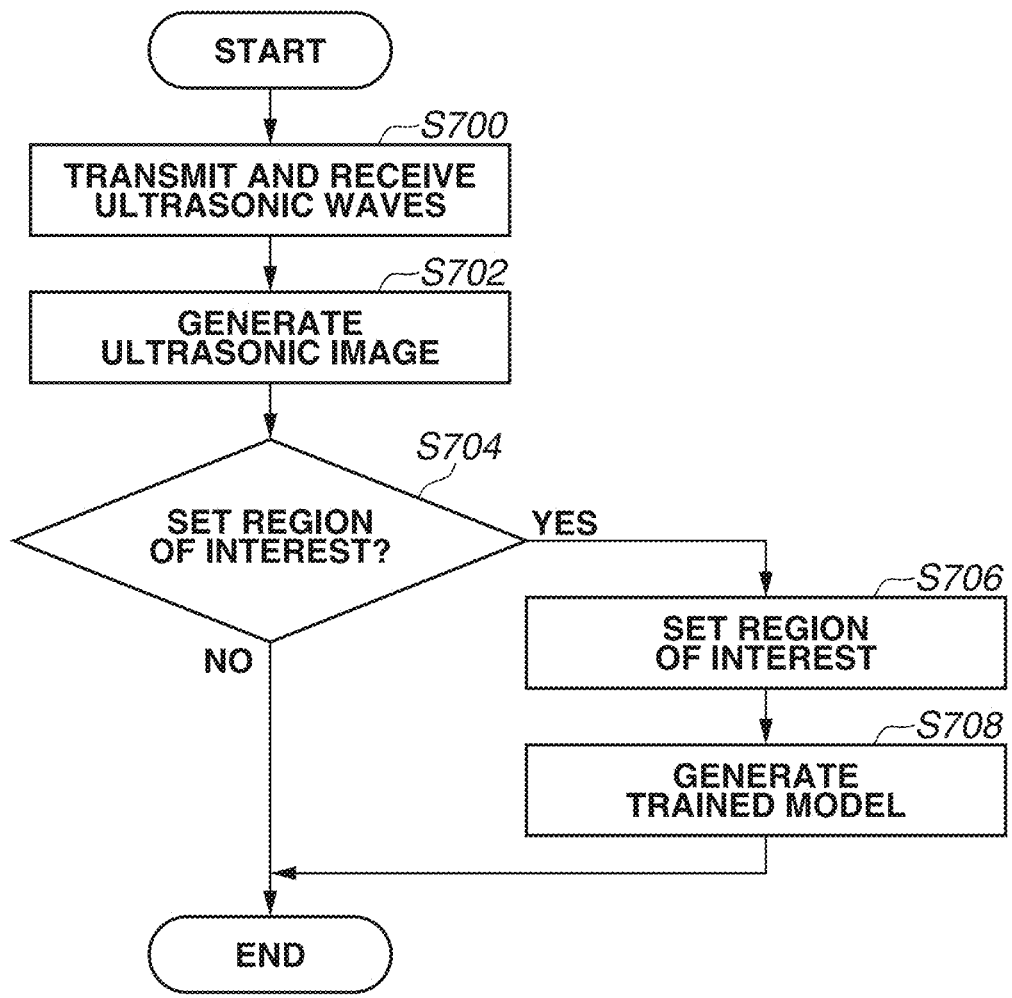
FIG. 7 is a flowchart illustrating an operation of the ultrasonic diagnostic apparatus according to the present exemplary embodiment in a training phase.

An operation of the ultrasonic diagnostic apparatus in the training phase will be described with reference to FIG. 7.

In step S700, the operator brings the ultrasonic probe 100 into contact with the subject. The ultrasonic probe 100 may be put in contact with the subject via ultrasonic gel. With the ultrasonic probe 100 in contact with the subject, the transmission and reception unit 110 makes the ultrasonic probe 100 transmit and receive ultrasonic waves.

In step S702, the ultrasonic image generation unit 112 performs various types of signal processing on an ultrasonic wave signal generated from the reflected wave signal by the transmission and reception unit 110 to generate an ultrasonic image.

In step S704, the operator determines whether to set a region of interest on the ultrasonic image via the operation unit 104 (region of interest setting unit 116). Here, whether to set a region of interest on the ultrasonic image may be determined based on the imaging mode. For example, if the imaging mode is the blood flow mode (CFM), a region of interest is determined to be set on the ultrasonic image via the operation unit 104 (region of interest setting unit 116). If a region of interest is determined to be set on the ultrasonic image (YES in step S704), the processing proceeds to step S706. If a region of interest is determined not to be set on the ultrasonic image (NO in step S704), the operation in the training phase ends.

In step S706, the region of interest setting unit 116 sets a region to generate a blood flow image as a region of interest on the ultrasonic image generated by the ultrasonic image generation unit 112. The region of interest (region coordinates) set by the region of interest setting unit 116 is transmitted to the training device 200 and the blood flow image generation unit 114.

In step S708, the training device 200 generates a trained data by performing training with the region of interest set on the ultrasonic image as teaching data. The training device 200 may generate the trained model by performing training with a blood flow region of the ultrasonic image and a region of interest on the blood flow region as teaching data. After step S708, the operation in the training phase ends.

Figure 8:
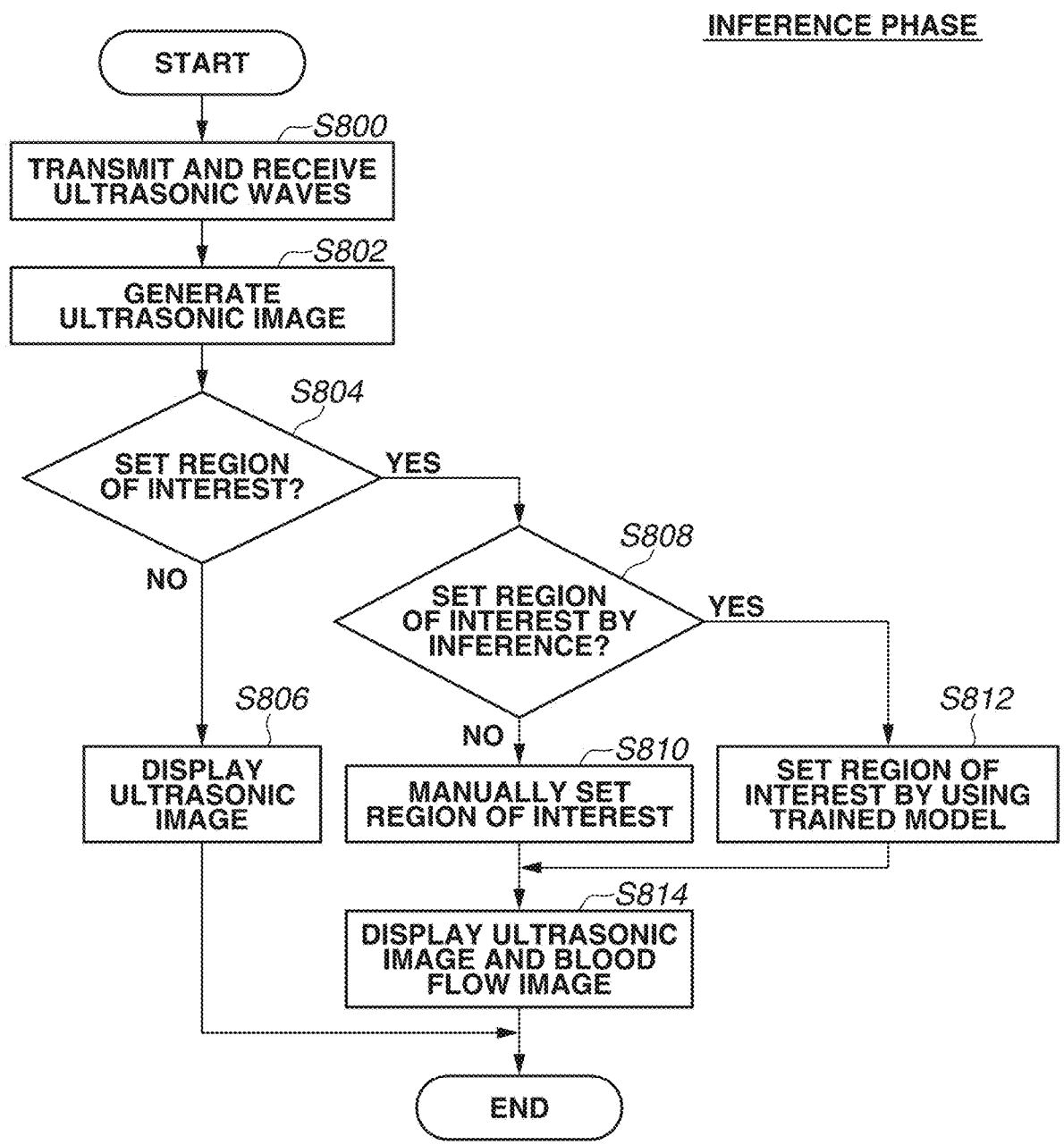
FIG. 8 is a flowchart illustrating an operation of the ultrasonic diagnostic apparatus according to the present exemplary embodiment in an inference phase.

Next, an operation of the ultrasonic diagnostic apparatus in the inference phase will be described with reference to FIG. 8.

In step S800, the operator brings the ultrasonic probe 100 into contact with the subject. With the ultrasonic probe 100 in contact with the subject, the transmission and reception unit 110 makes the ultrasonic probe 100 transmit and receive ultrasonic waves.

In step S802, the ultrasonic image generation unit 112 performs various types of signal processing on an ultrasonic wave signal generated from the reflected wave signal by the transmission and reception unit 110 to generate an ultrasonic image.

In step S804, the operator determines whether to set a region of interest on the ultrasonic image via the operation unit 104 (region of interest setting unit 116). Here, whether to set a region of interest on the ultrasonic image may be determined based on the imaging mode. If a region of interest is determined to be set on the ultrasonic image (YES in step S804), the processing proceeds to step S808. If a region of interest is determined not to be set on the ultrasonic image (NO in step S804), the processing proceeds to step S806.

In step S806, the display unit 106 displays only the ultrasonic image generated by the ultrasonic image generation unit 112. After step S806, the operation in the inference phase ends.

In step S808, the operator determines whether to set the region of interest by inference via the operation unit 104 (region of interest setting unit 116). For example, as illustrated in FIG. 6, the operator selects either one of the inferential setting button 604 and the manual setting button 606. If the region of interest is determined to be set by inference (YES in step S808), the processing proceeds to step S812. If the region of interest is determined not to be set by inference (NO in step S808), the processing proceeds to step S810.

In step S810, i.e., if the manual setting button 606 is pressed by the operator, the operator manually sets the region of interest 602 via the operation unit 104 (region of interest setting unit 116) while observing the blood flow region of the ultrasonic image 600.

In step S812, the inference unit 208 sets the region of interest 602 on the ultrasonic image displayed on the display unit 106 by using the trained model trained to set a region of interest on an ultrasonic image. The region of interest 602 set by the inference unit 208 is transmitted to the blood flow image generation unit 114.

In step S814, the blood flow image generation unit 114 generates a blood flow image for the region of interest by using the color Doppler method. The display unit 106 displays the blood flow image generated by the blood flow image generation unit 114 as superimposed on the ultrasonic image generated by the ultrasonic image generation unit 112. After step S814, the operation in the inference phase ends.

As described above, the ultrasonic diagnostic apparatus according to the present exemplary embodiment includes the ultrasonic image generation unit 112, the inference unit 208, and the display unit 106. The ultrasonic image generation unit 112 generates an ultrasonic image of a subject. By using a trained model trained with a region of interest set on the ultrasonic image (first ultrasonic image) as teaching data, the inference unit 208 sets a region of interest on a new generated ultrasonic image (second ultrasonic image). The display unit 106 displays the region of interest set by the inference unit 208 along with the new generated ultrasonic image (second ultrasonic image). The first ultrasonic image is an ultrasonic image captured in the past and on which a region of interest is set. The second ultrasonic image is an ultrasonic image displayed on the display unit 106.

An ultrasonic image display method according to the present exemplary embodiment includes generating an ultrasonic image of a subject, setting, by using a trained model trained with a region of interest set on the ultrasonic image (first ultrasonic image) as teaching data, a region of interest on a new generated ultrasonic image (second ultrasonic image), and displaying the set region of interest along with the new generated ultrasonic image (second ultrasonic image).

The region of interest can thus be quickly set on the new generated ultrasonic image (second ultrasonic image) by using the trained model trained with the region of interest set on the ultrasonic image (first ultrasonic image) as the teaching data.

An ultrasonic diagnostic apparatus according to a second exemplary embodiment of the present invention will be described with reference to FIGS. 9 and 10. The difference from the first exemplary embodiment is that a region of interest is set by a region of interest setting unit 116 (inference unit 208) and a transmission and reception direction of ultrasonic waves is set by a transmission and reception direction setting unit 900.

Figure 9:
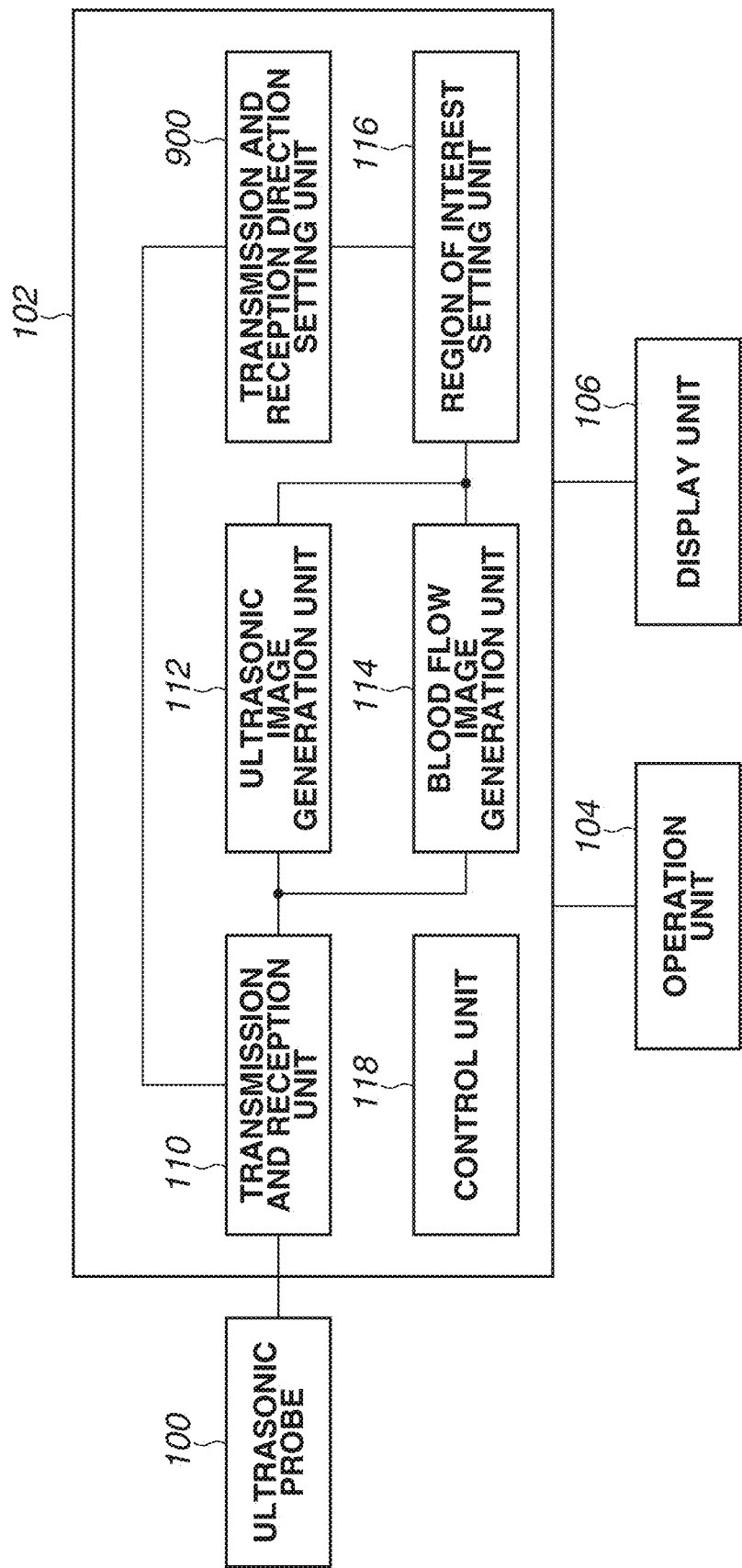
FIG. 9 is a diagram illustrating a configuration of an ultrasonic diagnostic apparatus according to a second exemplary embodiment of the present invention.
Figure 10:
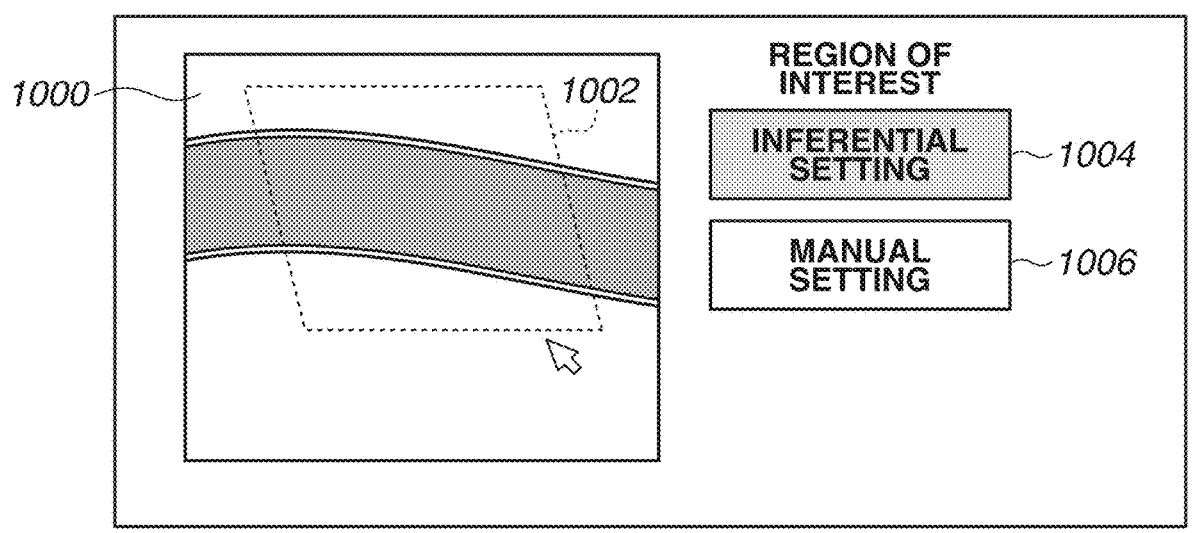
FIG. 10 is a diagram illustrating a display mode of a display unit of the ultrasonic diagnostic apparatus according to the present exemplary embodiment.

FIG. 9 is a diagram illustrating a configuration of the ultrasonic diagnostic apparatus according to the second exemplary embodiment of the present invention. As illustrated in FIG. 9, an apparatus main body 102 includes a transmission and reception unit 110, an ultrasonic image generation unit 112, a blood flow image generation unit 114, the region of interest setting unit 116, the transmission and reception direction setting unit 900, and a control unit 118. The transmission and reception unit 110 makes an ultrasonic probe 100 transmit and receive ultrasonic waves. The ultrasonic image generation unit 112 generates an ultrasonic image by using an ultrasonic wave signal received by the transmission and reception unit 110. The blood flow image generation unit 114 generates a blood flow image by using the ultrasonic wave signal received by the transmission and reception unit 110. The region of interest setting unit 116 sets a region of interest on the ultrasonic image. The transmission and reception direction setting unit 900 sets the transmission and reception direction of ultrasonic waves for generating a blood flow image based on the region of interest set by the region of interest setting unit 116 (inference unit 208). The control unit 118 controls various components of the apparatus main body 102.

FIG. 9 differs from FIG. 1 in the transmission and reception direction setting unit 900. The other components in FIG. 9 are similar to those in FIG. 1. The region of interest setting unit 116 according to the present exemplary embodiment is similar to that illustrated in FIGS. 2 and 3.

A new ultrasonic image generated by the ultrasonic image generation unit 112 is output to the region of interest setting unit 116 (inference unit 208). The region of interest setting unit 116 (inference unit 208) sets a region of interest on the new generated ultrasonic image by using a trained model trained to set a region of interest on an ultrasonic image.

Setting information (shape) about the region of interest on the new generated ultrasonic image is output to the transmission and reception direction setting unit 900. Ultrasonic waves intended for a blood flow image are tilted (steered) at a predetermined angle based on the setting information about the region of interest. The transmission and reception direction setting unit 900 makes a setting so that the ultrasonic waves intended for a blood flow image are steered at a predetermined angle based on the setting information about the region of interest. The transmission and reception unit 110 transmits and receives ultrasonic waves steered at a predetermined angle.

A display mode of a display unit 106 of the ultrasonic diagnostic apparatus will be described with reference to FIG. 10. As illustrated in FIG. 10, a region of interest 1002 set on a new generated ultrasonic image 1000 is tilted into a parallelogram shape. The ultrasonic waves intended for a blood flow image are tilted (steered) at a predetermined angle based on the parallelogram shape. The display unit 106 displays an inferential setting button 1004 for setting a region of interest by inference and a manual setting button 1006 for manually setting a region of interest. The inferential setting button 1004 and the manual setting button 1006 are similar to the inferential setting button 604 and the manual setting button 606 in FIG. 6. A description thereof will thus be omitted.

The region of interest 1002 set by the region of interest setting unit 116 (inference unit 208) is transmitted to the blood flow image generation unit 114. The blood flow image generation unit 114 generates a blood flow image for the region of interest 1002 set by the region of interest setting unit 116 by the color Doppler method. The display unit 106 displays the blood flow image generated by the blood flow image generation unit 114 as superimposed on the ultrasonic image generated by the ultrasonic image generation unit 112.

An ultrasonic diagnostic apparatus according to a third exemplary embodiment of the present invention will be described with reference to FIGS. 11 and 12. A difference from the first and second exemplary embodiments is that a trained model is generated by performing training with a region of interest on an elastic image as teaching data. Specifically, a training device 200 generates a trained model by performing training with a region of interest on a low echo region of an ultrasonic image as teaching data.

Figure 11:
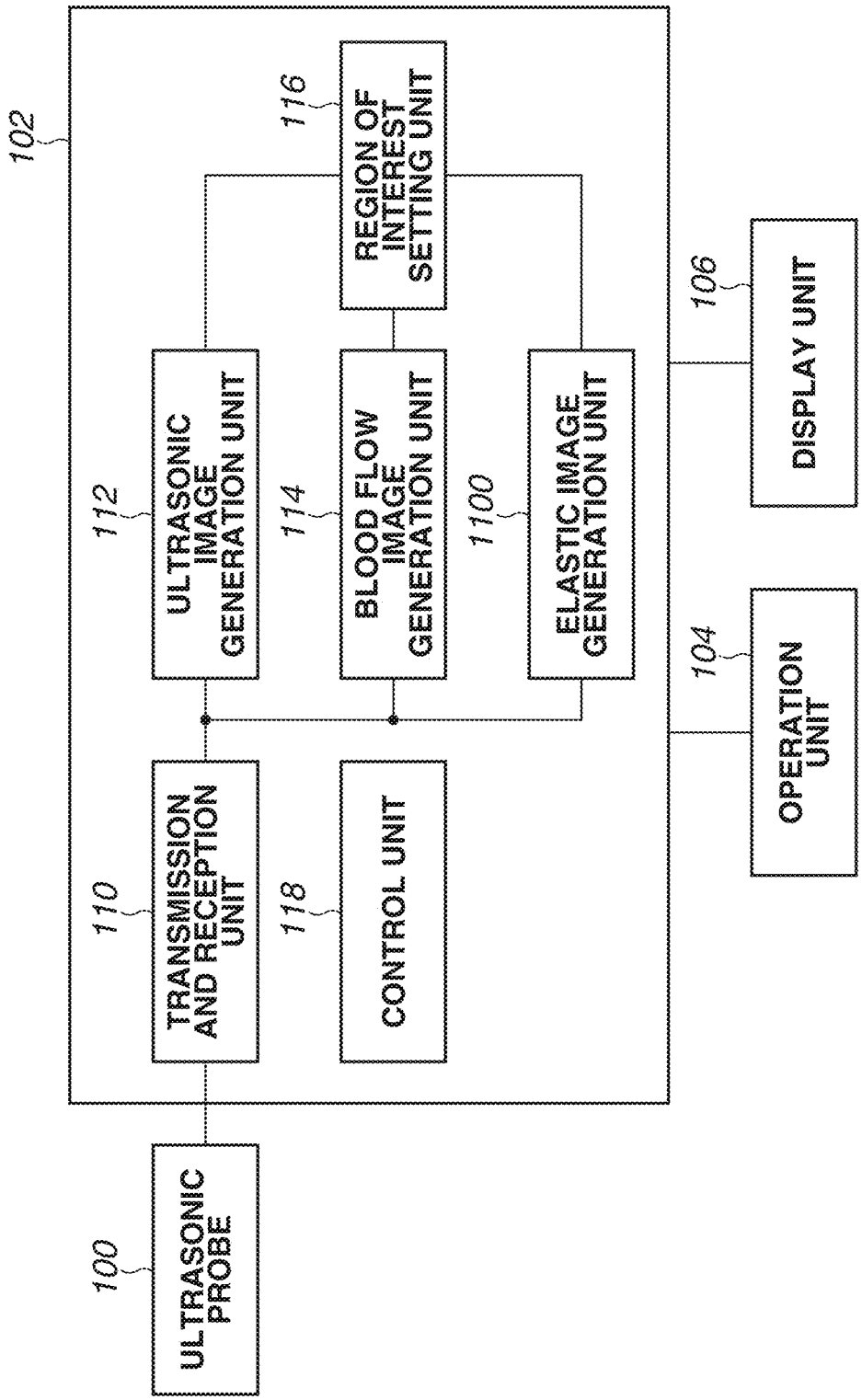
FIG. 11 is a diagram illustrating a configuration of an ultrasonic diagnostic apparatus according to a third exemplary embodiment of the present invention.
Figure 12:
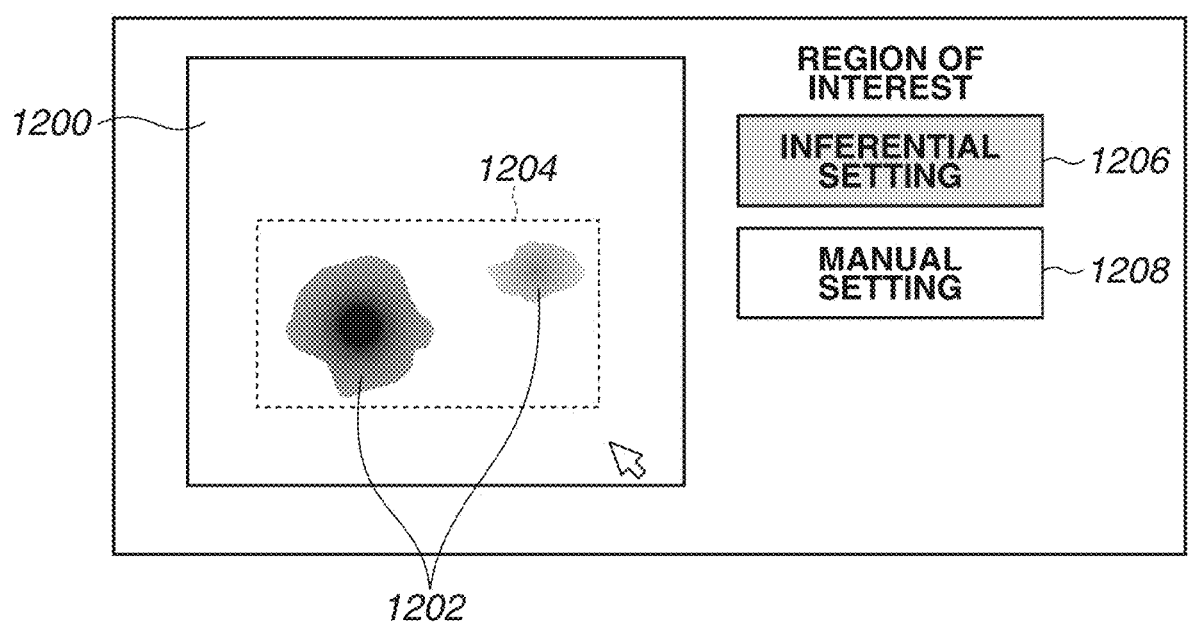
FIG. 12 is a diagram illustrating a display mode of a display unit of the ultrasonic diagnostic apparatus according to the present exemplary embodiment.

FIG. 11 is a diagram illustrating a configuration of the ultrasonic diagnostic apparatus according to the third exemplary embodiment of the present invention. As illustrated in FIG. 11, an apparatus main body 102 includes a transmission and reception unit 110, an ultrasonic image generation unit 112, a blood flow image generation unit 114, an elastic image generation unit 1100, a region of interest setting unit 116, and a control unit 118. The transmission and reception unit 110 makes an ultrasonic probe 100 transmit and receive ultrasonic waves. The ultrasonic image generation unit 112 generates an ultrasonic image by using an ultrasonic wave signal received by the transmission and reception unit 110. The blood flow image generation unit 114 generates a blood flow image by using the ultrasonic wave signal received by the transmission and reception unit 110. The elastic image generation unit 1100 generates an elastic image by using the ultrasonic wave signal received by the transmission and reception unit 110. The region of interest setting unit 116 sets a region of interest on the ultrasonic image. The control unit 118 controls various components of the apparatus main body 102.

FIG. 11 differs from FIG. 1 in the elastic image generation unit 1100. The other components in FIG. 11 are similar to those in FIG. 1. The region of interest setting unit 116 according to the present exemplary embodiment is similar to that illustrated in FIGS. 2 and 3.

The elastic image generation unit 1100 calculates distortion of tissue by performing a predetermined calculation (spatial differentiation) on displacements determined from a plurality of ultrasonic wave signals received by the transmission and reception unit 110. The elastic image generation unit 1100 can generate an elastic image based on distortion distribution information by rendering local distortion values of the tissue in color. The harder the tissue, the less likely to deform. Hard tissue thus has small distortion values. Softer living tissue has large distortion values. In other words, the distortion values indicate the hardness of the tissue. In an elastic mode, for example, the operator vibrates the ultrasonic probe 100 contacting the body surface of the subject to compress the tissue so that the tissue is deformed. The tissue can also be deformed by the application of force using an acoustic radiation pressure.

The training device 200 may generate a trained model by performing training with a low echo region (low luminance region) of an ultrasonic image and a region of interest on the low echo region as teaching data. Here, the training device 200 trains the model to learn the region of interest in association with the low echo region of the ultrasonic image. The reason is that the low echo region of the ultrasonic image is a region where a tumor can exist and hardness inspection using an elastic image may be desirable.

A display mode of a display unit 106 of the ultrasonic diagnostic apparatus will be described with reference to FIG. 12. In the elastic mode for displaying an elastic image, the region of interest setting unit 116 (inference unit 208) sets a region of interest 1204 on low echo regions 1202.

The region of interest setting unit 116 (inference unit 208) identifies a low echo region or regions in a new generated ultrasonic image and sets a region of interest on the low echo region(s) by using the trained model.

The region of interest 1204 set by the region of interest setting unit 116 (inference unit 208) is transmitted to the elastic image generation unit 1100. The elastic image generation unit 1100 generates an elastic image for the region of interest 1204 set by the region of interest setting unit 116. The display unit 106 displays the elastic image generated by the elastic image generation unit 1100 as superimposed on the ultrasonic image generated by the ultrasonic image generation unit 112.

In the training phase, the training device 200 of the region of interest setting unit 116 can determine whether a region of interest is set on an ultrasonic image frozen on the display unit 106, based on the ultrasonic imaging mode. For example, if the ultrasonic imaging mode is the blood flow mode (CFM) or the elastic mode (elastographic mode), the training device 200 can determine that a region of interest is set on the ultrasonic image. If a region of interest is determined to be set on the ultrasonic image, the training device 200 generates a trained model by performing training with the region of interest on the ultrasonic image as teaching data.

The inference unit 208 of the region of interest setting unit 116 may set a region of interest on a new generated ultrasonic image based on the imaging mode selected by the operator. If the operator selects the blood flow mode (CFM) or the elastic mode (elastographic mode) by the operation unit 104, the inference unit 208 sets a region of interest on an ultrasonic image generated in the blood flow mode (CFM) or the elastic mode (elastographic mode).

Specifically, if the operator selects the blood flow mode for displaying a blood flow image by the operation unit 104, information indicating the selection of the blood flow mode by the operation unit 104 is transmitted to the region of interest setting unit 116 (inference unit 208). The inference unit 208 sets a region of interest intended for a blood flow image on a blood flow region of a new generated ultrasonic image by using a trained model trained to set a region of interest intended for a blood flow image on an ultrasonic image.

If the operator selects the elastic mode for displaying an elastic image by the operation unit 104, information indicating the selection of the elastic mode by the operation unit 104 is transmitted to the region of interest setting unit 116 (inference unit 208). The inference unit 208 sets a region of interest intended for an elastic image on a new generated ultrasonic image by using a trained model trained to set a region of interest intended for an elastic image on an ultrasonic image.

An exemplary embodiment of the present invention can be applied to a medical imaging apparatus other than an ultrasonic diagnostic apparatus. Examples of the medical imaging apparatus other than an ultrasonic diagnostic apparatus include an ophthalmic apparatus. An ophthalmic apparatus can obtain a tomographic image of an eye to be inspected and use a Doppler signal obtained from interference light received by a light receiving element.

The ophthalmic apparatus according to the present exemplary embodiment includes an image generation unit, an inference unit, and a display unit. The image generation unit generates a tomographic image of an eye to be inspected. By using a trained model trained with a region of interest set on the tomographic image (first tomographic image) as teaching data, the inference unit sets a region of interest on a new generated tomographic image (second tomographic image). The display unit displays the region of interest set by the inference unit along with the new generated tomographic image (second tomographic image). In other words, a medical imaging apparatus according to the present exemplary embodiment includes a medical image generation unit, an inference unit, and a display unit. The medical image generation unit generates a medical image of a subject. By using a trained model trained with a region of interest set on the medical image (first medical image) as teaching data, the inference unit sets a region of interest on a new generated medical image (second medical image). The display unit displays the region of interest set by the inference unit along with the new generated medical image (second medical image). A computer program for implementing the functions of the first to third exemplary embodiments can be supplied to a computer via a network or a storage medium (not illustrated) and can be executed. The computer program is intended to cause the computer to perform the foregoing ultrasonic image display method. In other words, the computer program is a program for implementing the functions of an ultrasonic diagnostic apparatus with the computer. The storage medium stores the computer program.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-215796, filed Nov. 28, 2019, which is hereby incorporated by reference herein in its entirety.

What is claimed is:

1. An ultrasonic diagnostic apparatus comprising:
a memory storing a program; and
one or more processors which, by executing the program, function as:
an ultrasonic image generation unit configured to generate a first brightness mode image of a subject;
an inference unit configured to infer a region of interest on the first brightness mode image generated by the brightness mode image generation unit by using a trained model trained with a region of interest to cover on a blood flow region and a surrounding region of the blood flow region on a second brightness mode image by using teaching data including the blood flow region of the second brightness mode image and the region of interest set on the second brightness mode image, wherein the trained model is used for identifying a blood flow region from the first brightness mode image and setting the region of interest on the first brightness mode image;
a blood flow image generation unit configured to generate a blood flow image in the region of interest inferred by the inference unit; and
a display unit configured to display at least one of the blood flow image and the first brightness mode image generated by the ultrasonic image generation unit.

2. The ultrasonic diagnostic apparatus according to claim 1, further comprising a training device configured to generate the trained model by performing training with the region of interest on the second brightness mode image as the teaching data.

3. The ultrasonic diagnostic apparatus according to claim 2, wherein the training device is configured to generate the trained model by performing training with the blood flow region in the second brightness mode image and the region of interest on the blood flow region as the teaching data.

4. The ultrasonic diagnostic apparatus according to claim 2, wherein in a case where a region of interest is set on an ultrasonic image frozen on the display unit, the first brightness mode image displayed on the display unit and the region of interest are output to the training device.

5. The ultrasonic diagnostic apparatus according to claim 2, wherein the training device is configured to determine whether a region of interest is set on a brightness mode image frozen on the display unit, based on an ultrasonic imaging mode.

6. The ultrasonic diagnostic apparatus according to claim 5, wherein the training device is configured to determine that the region of interest is set on the first brightness mode image in a case where the ultrasonic imaging mode is a blood flow mode or an elastic mode.

7. The ultrasonic diagnostic apparatus according to claim 2, wherein the training device is configured to generate the trained model by training a neural network in association with the region of interest on the second brightness mode image as the teaching data.

8. The ultrasonic diagnostic apparatus according to claim 2, further comprising a storage unit configured to store the trained model generated by the training device.

9. The ultrasonic diagnostic apparatus according to claim 2, wherein the training device is installed outside the ultrasonic diagnostic apparatus.

10. The ultrasonic diagnostic apparatus according to claim 9, wherein the training device is configured to perform training with regions of interest set by a plurality of ultrasonic diagnostic apparatuses as the teaching data.

11. The ultrasonic diagnostic apparatus according to claim 1, wherein the inference unit is configured to identify the blood flow region on the first brightness mode image and set the region of interest on the blood flow region by using the trained model.

12. The ultrasonic diagnostic apparatus according to claim 1, further comprising a transmission and reception direction setting unit configured to set a transmission and reception direction of an ultrasonic wave for generating the blood flow image based on the region of interest inferred by the inference unit.

13. The ultrasonic diagnostic apparatus according to claim 2, wherein the training device is configured to generate the trained model by performing training with a low echo region in the second brightness mode image and a region of interest on the low echo region as the teaching data.

14. The ultrasonic diagnostic apparatus according to claim 1, wherein the inference unit is configured to identify a low echo region on the second brightness mode image and set the region of interest on the low echo region by using the trained model.

15. An ultrasonic image display method comprising:
generating a first brightness mode image of a subject;
inferring a region of interest on the first brightness mode image by using a trained model trained with a region of interest to cover on a low echo region and a surrounding region of the low echo region on a second brightness mode image by using teaching data including low echo regions of the second brightness mode image and regions of interest set on the second brightness mode image, wherein the trained model is used for identifying a low echo region from the first brightness mode image and setting the region of interest on the first brightness mode image;
generating a blood flow image in the inferred region of interest; and
displaying at least one of the blood flow image in the region of interest as and the first brightness mode image.

16. A storage medium storing a program for causing a computer to perform the ultrasonic image display method according to claim 15.

17. The ultrasonic diagnostic apparatus according to claim 1,
wherein the display unit displays an inferential setting icon for setting the region of interest by inference and a manual setting icon for setting the region of interest manually, and wherein, in a case where the inferential setting icon is selected by an operator, the inference unit infers the region of interest on the ultrasonic image by using the trained model, and in a case where the manual setting icon is selected by the operator, the region of interest is set manually by the operator via an operation unit.

18. An ultrasonic diagnostic apparatus comprising:
a memory storing a program; and
one or more processors which, by executing the program, function as:
an ultrasonic image generation unit configured to generate a first brightness mode image of a subject;
an operation unit configured to select either an image mode of a blood flow mode or an elastic mode;
an inference unit configured to infer a first region of interest on the first brightness mode image generated by the ultrasonic image generation unit by using a first trained model trained with a first region of interest on a blood flow region of a second brightness mode image by using teaching data including the blood flow region of the second brightness mode image and the first region of interest set on the second brightness mode image, in the case where the blood flow mode for displaying a blood flow image is selected by the operation unit, wherein the first trained model is used for identifying the blood flow region from the first brightness mode image and setting the first region of interest on the first brightness mode image;
an image generation unit configured to generate a blood flow image in the first region of interest inferred by the inference unit; and
a display unit configured to display the blood flow image in the first region of interest inferred by the inference unit as superimposed on the first brightness mode image generated by the ultrasonic image generation unit,
wherein the inference unit infers a second region of interest on the first brightness mode image generated by the ultrasonic image generation unit by using a second trained model trained with a second region of interest on an elastic region of a third brightness mode image by using teaching data including the elastic region of the third brightness mode image and the second region of interest set on the third brightness mode image, in the case where the elastic mode for displaying an elastic image is selected by the operation unit, wherein the second trained model is used for identifying the elastic region from the first brightness mode image and setting the second region of interest on the first brightness mode image;
wherein the image generation unit generates an elastic image in the second region of interest inferred by the inference unit; and
wherein the display unit displays the elastic image in the second region of interest inferred by the inference unit as superimposed on the first brightness mode image generated by the ultrasonic image generation unit.

* * * * *